United States Patent [19]

Huang et al.

[11] Patent Number: 5,696,327
[45] Date of Patent: Dec. 9, 1997

[54] METHOD AND APPARATUS FOR SEPARATING A THIN FILM FROM A SUBSTRATE

[75] Inventors: He Huang, Minneapolis; Maarten P. de Boer, St. Paul; John C. Nelson, Maplewood; Feng Wang, St. Paul; William W. Gerberich, Shorewood, all of Minn.

[73] Assignee: Regents of the University of Minnesota, Minneapolis, Minn.

[21] Appl. No.: 344,841

[22] Filed: Nov. 23, 1994

[51] Int. Cl.$^6$ .................................................. G01N 3/24
[52] U.S. Cl. ........................... 73/845; 73/150 A; 156/344
[58] Field of Search ................................ 156/344, 584; 73/794, 795, 842, 845, 150 A

[56] References Cited

U.S. PATENT DOCUMENTS

| | | | |
|---|---|---|---|
| 2,453,576 | 11/1948 | Jacob | 73/845 X |
| 4,183,751 | 1/1980 | Matsumoto et al. | 156/584 X |
| 4,346,602 | 8/1982 | Gould et al. | 73/842 |
| 4,421,586 | 12/1983 | Bargman | 156/584 X |
| 4,445,387 | 5/1984 | Hall et al. | 73/845 |
| 4,466,851 | 8/1984 | Hoffman | 156/344 |
| 4,687,152 | 8/1987 | Hawkswell | 156/584 |
| 4,738,386 | 4/1988 | Itemadani et al. | 156/584 X |
| 4,750,962 | 6/1988 | Haygood et al. | 156/344 X |
| 4,752,346 | 6/1988 | Platzer | 156/584 |
| 4,821,578 | 4/1989 | Brar et al. | 73/827 |
| 4,856,326 | 8/1989 | Tsukamoto | 73/150 A |
| 4,934,185 | 6/1990 | Nishiyama et al. | 73/105 A |
| 5,091,042 | 2/1992 | Bruckner | 156/584 |
| 5,333,967 | 8/1994 | Foley et al. | 156/584 X |
| 5,537,884 | 7/1996 | Mishimura et al. | 73/842 |
| 5,575,868 | 11/1996 | Mann | 156/64 |

FOREIGN PATENT DOCUMENTS

| | | | |
|---|---|---|---|
| 54-1088 | 1/1979 | Japan | 73/150 A |
| 3-188354 | 8/1991 | Japan | 73/842 |
| 448370 | 10/1974 | U.S.S.R. | |
| 896504 | 1/1982 | U.S.S.R. | |
| 1499163 A1 | 8/1989 | U.S.S.R. | |

OTHER PUBLICATIONS

"Adhesion Measurement of Thin Films", K.L. Mittal, *Electrocomponent Science and Technology*, 1976, vol. 3, pp. 21–42.

"Adhesion of Non–Selective CVD Tungsten to Silicon Dioxide", D. Woodruf, R. Wilson, and R. Sanchez–Marinez, General Electric Corporate Research and Development, Schenectady, NY 12301, 1985 Materials Research Society, pp. 173–183.

"Failure Mode Analysis of TiN–Coated High Speed Steel: In Situ Scratch Adhesion Testing in the Scanning Electron Microscope", P. Hedenqvist et al., published by Elsevier Sequoia, 1990.

"Use of the microindentation technique for determining interfacial fracture energy", L.G. Rosenfeld et al., *J. Appl. Phys.*, vol. 67, No. 7, Apr. 1, 1990, pp. 3291–3296.

(List continued on next page.)

*Primary Examiner*—Mark A. Osele
*Attorney, Agent, or Firm*—Westman, Champlin & Kelly, P.A.; S. Koehler

[57] ABSTRACT

An apparatus and method for separating a thin film from a substrate, the thin film having a surface with a selected width, includes an indenter for applying a force to the surface of the thin film that is substantially equal along the selected width. The forces are applied until separation of a portion of the thin film from the substrate occurs. In a preferred embodiment, the indenter is made from a block of material having a substantially flat surface engageable with the surface of the thin film. The substantially flat surface of the block of material has a width at least equal to the width of the surface of the thin film. Based on the two dimensional geometry of the mechanics, accurate analysis of work of adhesion is achieved.

17 Claims, 6 Drawing Sheets

OTHER PUBLICATIONS

"Microscratch and load relaxation tests for ultra–thin films", T.W. Wu, *Journal of Material Research*, vol. 6, No. 2, Feb. 1991, pp. 407–426.

"Microscratch testing to characterize the adhesion of thin layers", C. Julia–Schmutz et al., published by Elsevier Sequoia, 1991, pp. 1–6.

"Microscratch analysis of work of adhesion for Pt thin films on NiO", S. Venkataraman et al., *Journal of Material Research*, vol. 7, No. 5, May 1992, pp. 1–7.

"Measurement of Thin Film Mechanical Properties Using Nanoindentation", G.M. Pharr et al., *Materials Research Society Bulletin*, Jul. 1992, pp. 28–32.

"Material response to two–dimensional scratching by wedges", S. Kailas et al., *Wear*, 162–164 (1993), pp. 110–118.

Brochure, *Romulus II*, "For Every Adhesion Test Need", Adhesion International, Spokane, WA.

5,696,327

1

METHOD AND APPARATUS FOR SEPARATING A THIN FILM FROM A SUBSTRATE

BACKGROUND OF THE INVENTION

The present invention relates to an apparatus and method for separating a thin film from a substrate. This invention was made with government support under DOE-DE-FG02-88ER-45337 awarded by the Department of Energy. The government has certain rights in the invention.

As used herein, adhesion will be defined in terms of work or energy done in separating or detaching two materials from one another. Commonly, this definition is called the "work of adhesion." The work of adhesion is represented by the following equation:

$$G = -\frac{\partial U}{\partial A}$$

wherein $\partial U$ is the strain energy required to separate a unit area of a surface given by $\partial A$.

The use of thin films in industry is increasing constantly. For example, thin films are used extensively in a variety of fields such as magnetic materials and electronic materials. Typically, the thin films are applied to a substrate and using known photolithography and etching techniques are formed into well defined thin film fine lines. Good adhesion of the thin film fine line to the substrate is essential for high yield and reliability in the corresponding product. Therefore, there has been continued development in the art to measure the work of adhesion of thin film/substrate specimens.

To date, the methods and apparatuses used to test the work of adhesion of thin films are typically tested on unetched films. These tests include direct pull-off methods wherein a pulling device such as brass pins are affixed to the thin film by means of soldering or an adhesive, and then the film is pulled in a direction perpendicular to its major planar surface by a tensile tester. Other techniques include application of a pressure sensitive tape to the film that is rapidly stripped away, while another includes bonding a microscope glass slide to the thin film and pulling on the slide in a direction parallel to the thin film to develop a shear force in the large bonded area.

In recent years, techniques such as the bulge test, the indentation test and the micro-scratch test have been explored to measure adhesion of thin films using a fracture mechanics approach. However, all of these tests, like the tests described above, are performed on unetched or planar thin film samples making correlation of the test results to real world application of thin film lines questionable. For these reasons, none of these techniques have shown universal applicability.

SUMMARY OF THE INVENTION

An apparatus and method for separating a thin film from a substrate, the thin film having a surface with a selected width, includes an indenter for applying a force to the surface of the thin film that is substantially equal along the selected width. The forces are applied until separation of a portion of the thin film from the substrate occurs. In a preferred embodiment, the indenter is made from a block of material having a substantially flat surface engageable with the surface of the thin film. The substantially flat surface of the block of material has a width at least equal to the width of the surface of the thin film.

In a further preferred embodiment, the block of material is wedge-shaped having a second surface on the side oppo-

2 site the substantially flat surface. The substantially flat surface and the second surface are inclined towards each other to form an apex that extends linearly a distance at least equal to the width of the thin film. Preferably, the apex comprises a narrow planar surface that adjoins the substantially flat surface and the second surface. By forming a narrow planar surface on the apex, the strength of the indenter is increased.

To analyze the work of adhesion of a thin film joined to a substrate, a specimen is prepared wherein a sample of the thin film is joined to the substrate, the sample of the thin film having a selected width. Using the indenter described above, or a similar device, a force is applied to the sample of the thin film, the force being substantially equal along the selected width. The force is applied to a portion of the thin film sample to separate the thin film from the substrate. By measuring a magnitude of the force while the force is applied and by measuring an area of the portion of the thin film that has separated, the work of adhesion between the thin film and the substrate can be calculated.

The present invention provides an improved apparatus and method for separating thin films from their corresponding substrates. By applying a force to a thin film line along its width and creating a shear plane that separates the thin film from the substrate, a more accurate and consistent calculation of the work of adhesion is obtained since side constraints on the thin film sample have been eliminated making for a substantially two dimensional geometry. The apparatus and method of the present invention is equally suited to analyze the work of adhesion for brittle, hard materials such as sputtered tungsten on silicon having a thermally grown silicon dioxide adhesive layer, as well as ductile materials deposited on soft polymers, for example, copper joined to PMDA-ODA polyimide. Both of these systems are used widely in the micro-electronics industry.

DETAILED DESCRIPTION OF THE PREFERRED EMBODIMENTS

Figure 1:
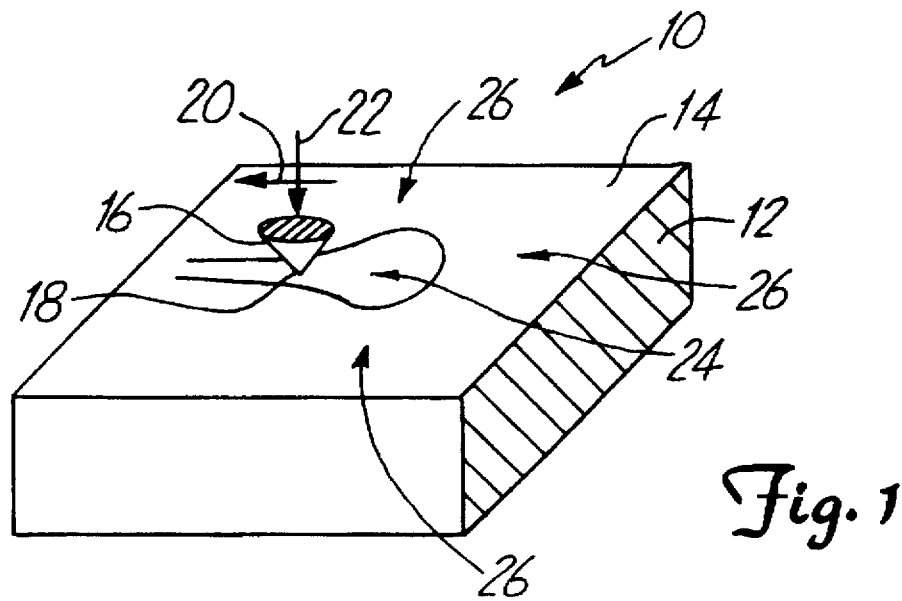
FIG. 1 is a schematic perspective view of a prior art apparatus for separating a thin film from a substrate.

Before discussing the present invention, a brief review of a conventional method and system for separating a thin film from a substrate will be helpful. FIG. 1 schematically illustrates such a prior art system at 10. The system 10 is commonly known as a point micro-scratch test. In the point micro-scratch test, scratches using a diamond stylus 16 are made on a thin film 14 that is joined to a substrate 12. The diamond stylus 16 is formed to have a sharp point 18, and commonly, is conical. During testing, the diamond stylus 16 remains stationary while the substrate 12 and the thin film 14 are displaced in a direction indicated by arrow 20. At the same time, a constant or an increasing normal load in a direction indicated by arrow 22 is applied until a load drop (critical load) is observed indicating that the thin film 14 has delaminated from the substrate 12.

Theoretical models are then used to calculate the work of adhesion by using the width of the scratch track at which the thin film 14 delaminated from the substrate 12, the critical load required for delamination, and the area of delamination in the damaged region 24. However, with a side constraint present from adjoining unaffected areas 26, analysis of the undamaged area 24 is difficult. For instance, with respect to modelling, stresses in the substrate 12 are only approximate due to the three dimensional nature of the damaged area 24. Likewise, even observation of the damaged area 24 can be difficult to determine since the thin film/substrate region is not directly observable. These problems are compounded when testing thin films joined to polymer substrates since three-dimensional loading configurations and the viscoelastic properties of polymers make it extremely difficult to obtain a clear delamination.

Figure 2:
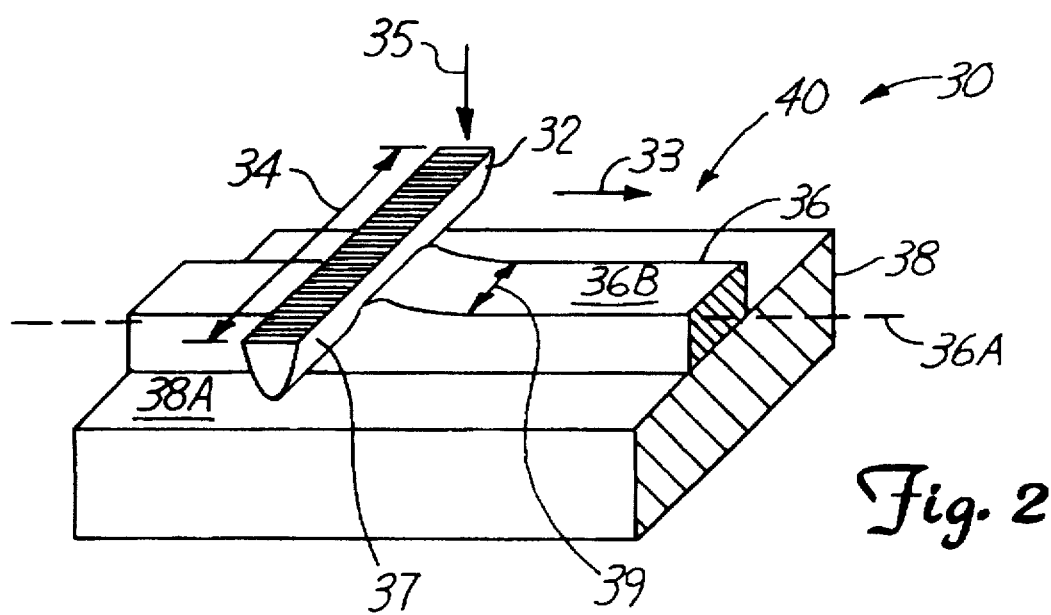
FIG. 2 is a schematic perspective view of an indenter of the present invention engaging a surface of the thin film.

FIG. 2 schematically illustrates a system 30 comprising an embodiment of the present invention. Generally, the system 30 includes a wedge-shaped indenter 32, preferably formed from diamond although other suitable strong materials such as sapphire could be used, having a lateral width indicated by double arrow 34. The wedge-shaped diamond indenter 32 is mounted to a force application structure, described below, and, in a first embodiment, provides a lateral force, as indicated by arrow 33, and downward force, as indicated by arrow 35, to engage a thin film line 36 that has been deposited or joined to a substrate 38, which together comprise a specimen 40. It should be understood that in the illustration of FIG. 2, and other figures discussed below, the thickness of the thin film line 36 has been exaggerated in order to enhance understanding of the present invention. Typically, the thin film line 36 is 0.1 micrometers to 10 micrometers thick although thinner and thicker thin films could also be tested using the present invention.

Figure 3:
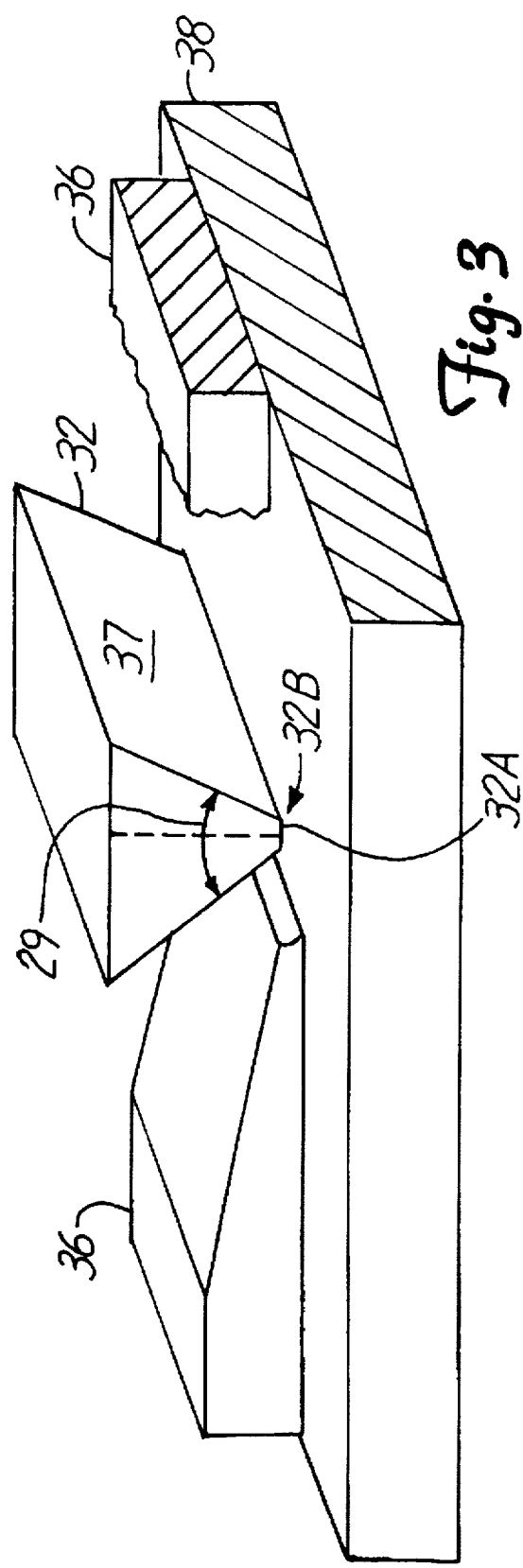
FIG. 3 is a perspective view of the indenter after delamination of the thin film.

The indenter 32 includes a substantially flat contact surface 37 so as to apply equal forces along a width 39 of the thin film 36. Since the lateral width 34 of the indenter 32 is selected so as to be at least as wide as the width 39 of the thin film 36, a shear plane is created that results in controlled delamination of the thin film 14 ahead of the indenter 32 as illustrated in FIG. 3.

The present invention is well suited to analyze the work of adhesion for a variety of thin films and substrate combinations. In a first example, sputtered tungsten is deposited on thermally grown silicon dioxide ($SiO_2$) over a silicon substrate. Standard integrated circuit processing is used to fabricate the thin film line 36. Briefly, silicon wafers were thermally oxidized at 1100° C. in steam to grow a 1.5 micrometer layer of silicon dioxide. Tungsten was then RF-sputter deposited to a thickness of 0.8 micrometers on the edge of the wafer and 1.0 micrometer at the center of the wafer. Conventional photolithography techniques were used to isolate fine lines and were etched in a 50° C. heated 30% hydrogen peroxide solution. The lines were approximately 10 micrometers wide with an overall length of 200 micrometers.

As stated above, the apparatus and method of the present invention preferably includes the wedge-shaped diamond indenter 32. The wedge-shaped diamond indenter 32 has a lateral width that is greater than the width of the fine line to be tested. Referring to FIG. 3, the wedge-shaped diamond indenter 32 has an included angle 29 of 90°, and, preferably, includes a flat horizontal surface 32A at an apex 32B. The lateral width is 20 micrometers and the horizontal surface is 0.7 micrometers. Formation of the horizontal surface 32A is preferred when a hard thin film, such as the tungsten described above, is to be tested since flattening increases the lateral strength of the wedge-shaped indenter 32. When provided with the specifications described above, Imetra, Inc. of Elmsford, N.Y., manufactured the indenter 32.

The indenter 32 was mounted to a continuous microindenter testing system, described below, with a load resolution of 16 micronewtons and depth resolution of 0.5 nanometers. Typically, the indent mark left by the indenter 32 was within 5 degrees of perpendicular to a longitudinal axis 36A of the thin film 14. Some tilt of the indenter 32 relative to a major surface plane 38A of the substrate 38 was also observed. The indenter 32 was simultaneously drawn along the thin film line 36 at 0.1 micrometers/sec, and driven into a line at 20 to 30 nanometers/sec.

Figure 4:
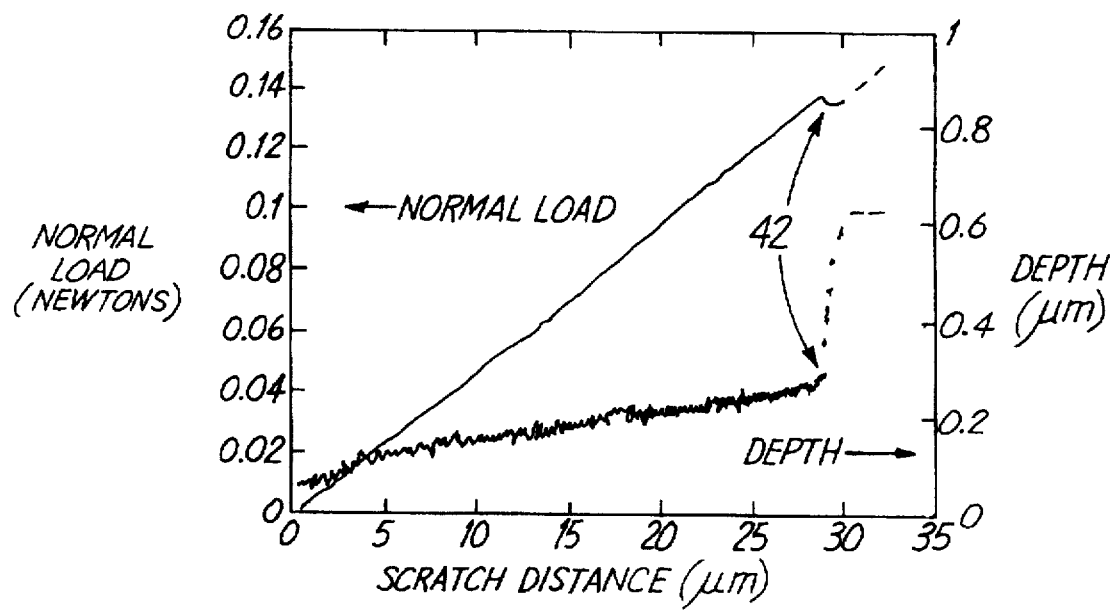
FIG. 4 is a graph illustrating loads applied to the thin film as a function of distance during testing.
Figure 5:
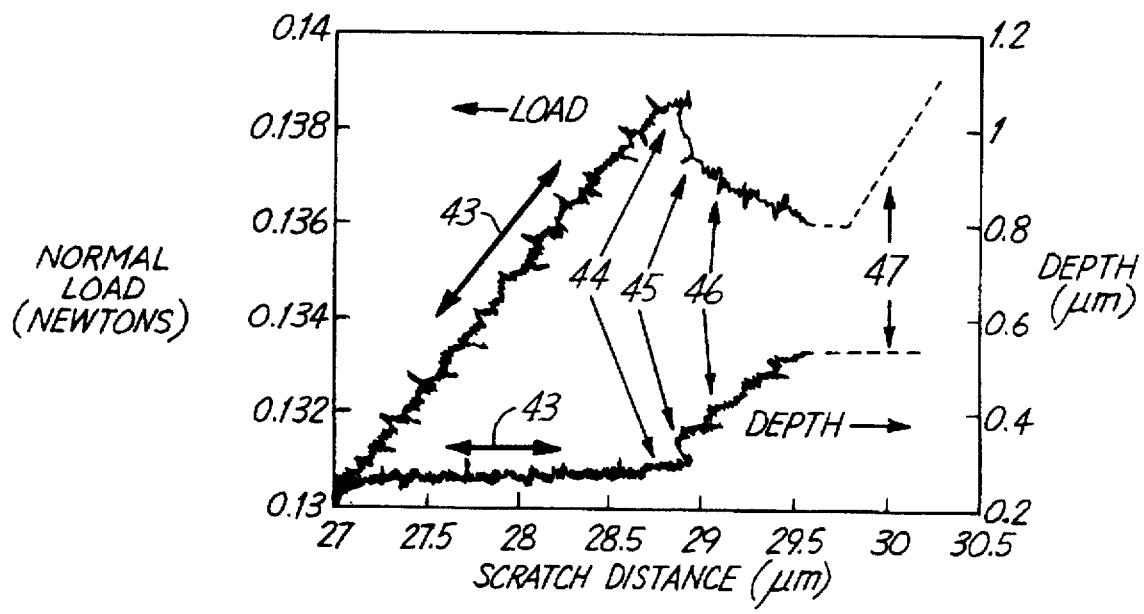
FIG. 5 is an enlarged portion of the graph of FIG. 4.

FIG. 4 illustrates the associated normal load versus scratch distance curve for the scratch test described above. FIG. 5 is an expanded graph of a region 42 in FIG. 2. Referring to FIG. 5, region 43 represents a region of relatively high load where cracking of the thin film line 36 occurs behind the indenter 32, but is not indicated by any characteristic in the load curve. Point 44 occurs just before catastrophic failure and is indicated by a minor change in slope for both the normal load and depth versus scratch distance. At point 45, a one millinewton reduction in the normal load value takes place in less than 80 milliseconds (as determined by the sampling rate). Lateral load, not shown, also shows a similar step in reduction, but its value is significantly larger at 2 to 3 millinewtons. After about 0.15 micrometers more of scratching at point 46, the load continues to reduce and the depth penetration increases significantly. By this time an interfacial crack has propagated and a portion of the thin film line 36 ahead of the indenter 32 has spalled. In region 47, the apex 32B of the indenter 32 strikes the substrate 38 and the normal load begins to rise again as the depth flattens out.

The work of adhesion can be calculated using a fundamental fracture mechanics approach. One skilled in the art will recognize that $$G = \frac{\sigma_{lat}^2 h}{2 E_f} F$$

where $$\sigma_{lat} = \left( \frac{P_{lat}}{bh} \right)$$

G=strain energy release rate
$\sigma_{lat}$=lateral stress (along the interfacial direction)
$P_{lat}$=lateral force
f subscript denotes the film b=width of the thin film h=thickness of the thin film, and $$E_f' = \frac{E_f}{1-v_f^2}$$

where $E_f$=Younge's Modulus $v_f$=Poisson's Ratio

When $G \geq G_c$ (the work of adhesion), the crack will propagate according to the Griffith criteria.

F is a modifying equation and includes:

$F=F(P_{lat}, P_{norm}, E_s, E_f, v_s, v_f, \mu, a, h, \ldots)$ where $P_{norm}$=normal force subscript denotes the substrate $\mu$ is the coefficient of friction between the thin film and the substrate near the indenter tip.

However, in the limiting case where a rigid substrate is present and the thickness of the thin film is much less than the length of the interfacial crack (h<<a), F is approximately=1. If desired, further detailed analysis of bimaterial linear elastic fracture mechanics can be used and are covered in detail by J. R. Rice, in J. Appl. Mech., 55, (1988) p. 98. and P. G. Charalambides, J. Lund, A. G. Evens and R. M. McMeeking, in ASME J. Appl. Mech., 56, (1988) p. 98.

Figure 6:
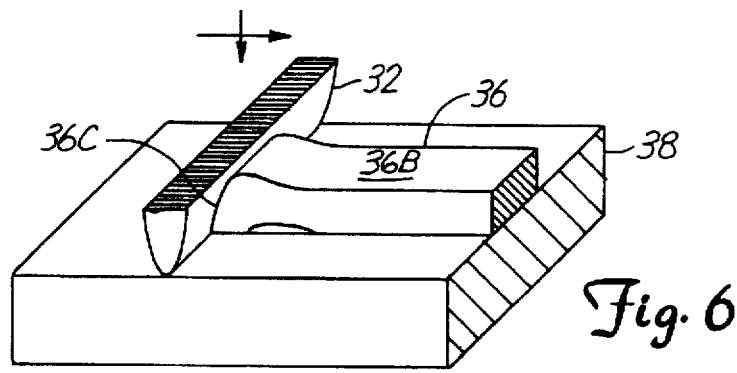
FIG. 6 is a schematic perspective view of the indenter of the present invention engaging a second surface of the thin film.

It should be understood that although FIG. 2 illustrates a method wherein initial contact is made with a major planar surface 36B of the thin film line 36, this method is not the only manner in which a portion of the thin film line 36 can be removed. As illustrated in FIG. 6, the indenter 32 can be positioned to contact an edge surface 36C of the thin film line 36 with the help of a suitable optical microscope or other positioning means. Contact in this manner, may be more effective in initiating interfacial fracture in some thin film/substrate specimens. Likewise, although not shown, a normal load upon the major surface 36B of the thin film line 36 without lateral displacement may also be sufficient to delaminate a portion of the thin film line 36 in yet other thin film/substrate specimens.

Figure 7:
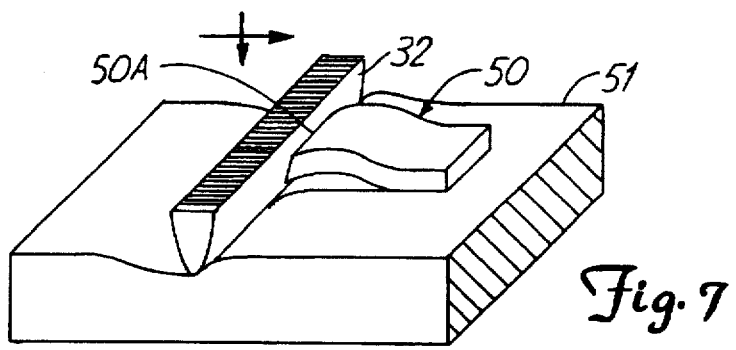
FIG. 7 is a schematic perspective view of the indenter of the present invention engaging a thin film block.
Figure 8:
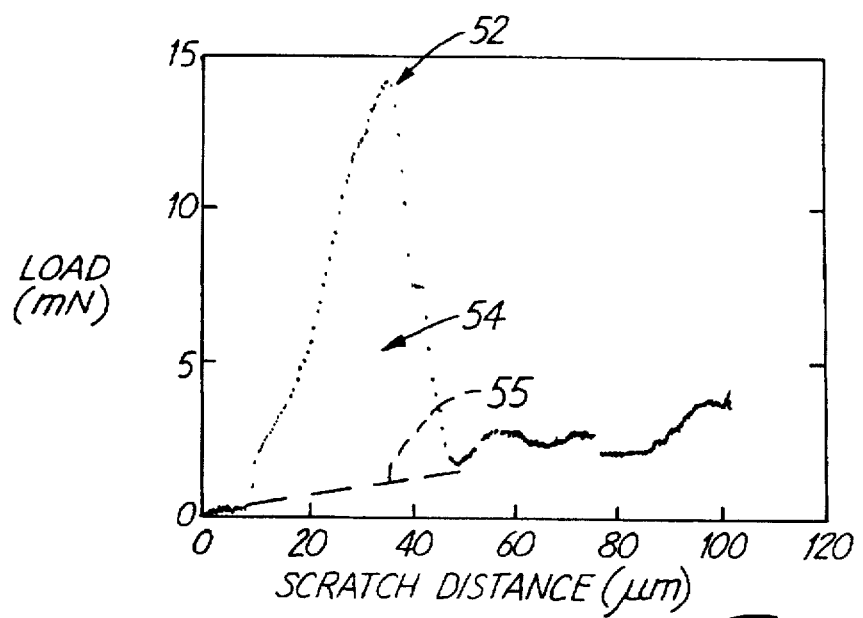
FIG. 8 is a graph illustrating loads applied to the thin film block as a function of distance during testing.

The method and apparatus of the present invention is also well suited for separating thin films from polymer substrates. In a second example, a 0.2 micrometer thick copper thin film was deposited on a 50 micrometer thick PMDA-ODA polyimide solid film using a RF planar magnetron sputtering system. After a sample had been spin-coated with a 1.8 micrometer layer of photoresist, ultra violet printing was performed using a suitable mask to obtain a thin film block 50 on a polyimide substrate 51, as illustrated in 7. In a preferred method of scratching, the indenter 32 was driven laterally at a constant depth to engage an end surface 50A of the thin film block 50. The normal load versus scratch distance of this method of testing is illustrated in FIG. 8. Initiation of delamination of the thin film block 50 from the polyimide substrate 51 is indicated at 52. The work due to delamination of the block 50 is indicated in region 54 that is above dashed line 55. Knowing the area of the block 50 in contact with the polyimide substrate 51, provides an estimate of the work of adhesion. The work of adhesion can also be calculated based on the fundamental fracture mechanics approach described above. Although the copper thin film was separated from the polyimide substrate using the method described and illustrated in FIG. 7, it should be understood that any of the other separation techniques described above could also be used. Further, the tungsten/silicon and copper/polyimide specimens have been chosen to illustrate the applicability of the present invention to a wide variety of thin film/substrate systems. The tungsten/silicon specimen illustrates applicability of the present invention to hard or brittle thin films joined to hard material substrates, while the copper/polyimide specimen illustrates applicability of the present invention to ductile thin films joined to soft or compliant substrates. These specimens should not be considered limiting in that the present invention is believed also applicable to hard thin films joined to soft substrates and soft thin films joined to hard substrates.

Figure 9:
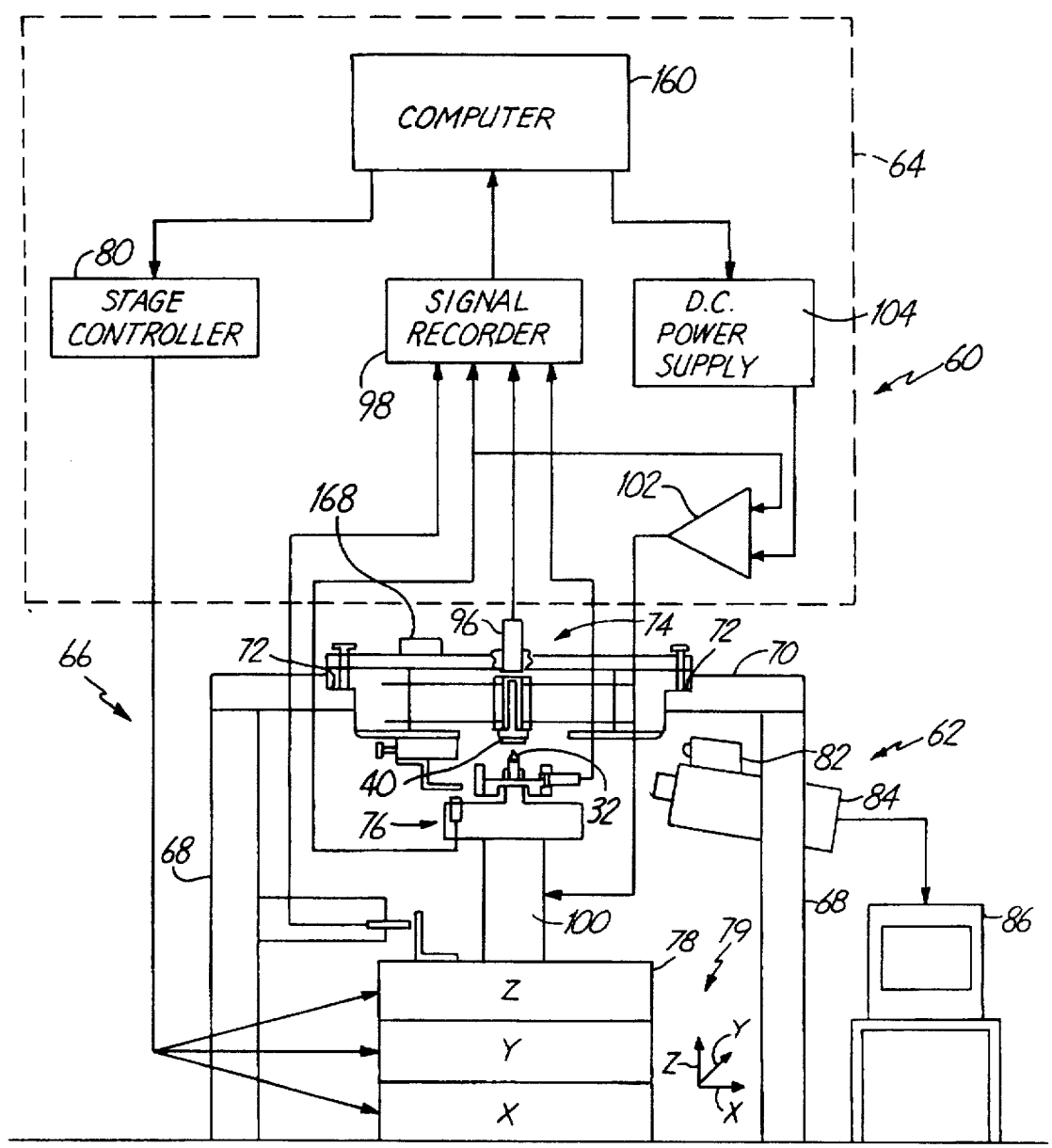
FIG. 9 is a schematic representation of a microindentation testing system including the indenter of the present invention.

FIG. 9 illustrates a microindentation testing system 60 for analyzing the work of adhesion of a thin film sample joined to a substrate and includes the indenter 32. Generally, the testing system 60 comprises a microindentation machine indicated at 62 and a controller indicated at 64. The microindentation machine 62 includes a frame 66 having vertical support columns 68 that support an upper platform 70. The upper platform 70 has extending flanges 72 that support a load cell assembly indicated at 74. The load cell assembly supports 74 the thin film/substrate specimen 40 over an indenter assembly 76 having the indenter 32. The indenter assembly 76 is mounted to a three-axis stage 78 that is capable of linear movements in directions parallel to three orthogonal axes indicated at 79. The stage assembly 78 receives control signals from a stage controller 80, which is used to position the indenter 32 proximate the thin film/substrate specimen 40. A light 82 is provided and illuminates the indenter 32 and the thin film/substrate specimen 40. A camera 84 monitors the indenter 32 and the thin film/substrate specimen 40, providing image signals to a suitable display 86 to aid in positioning.

Figure 10:
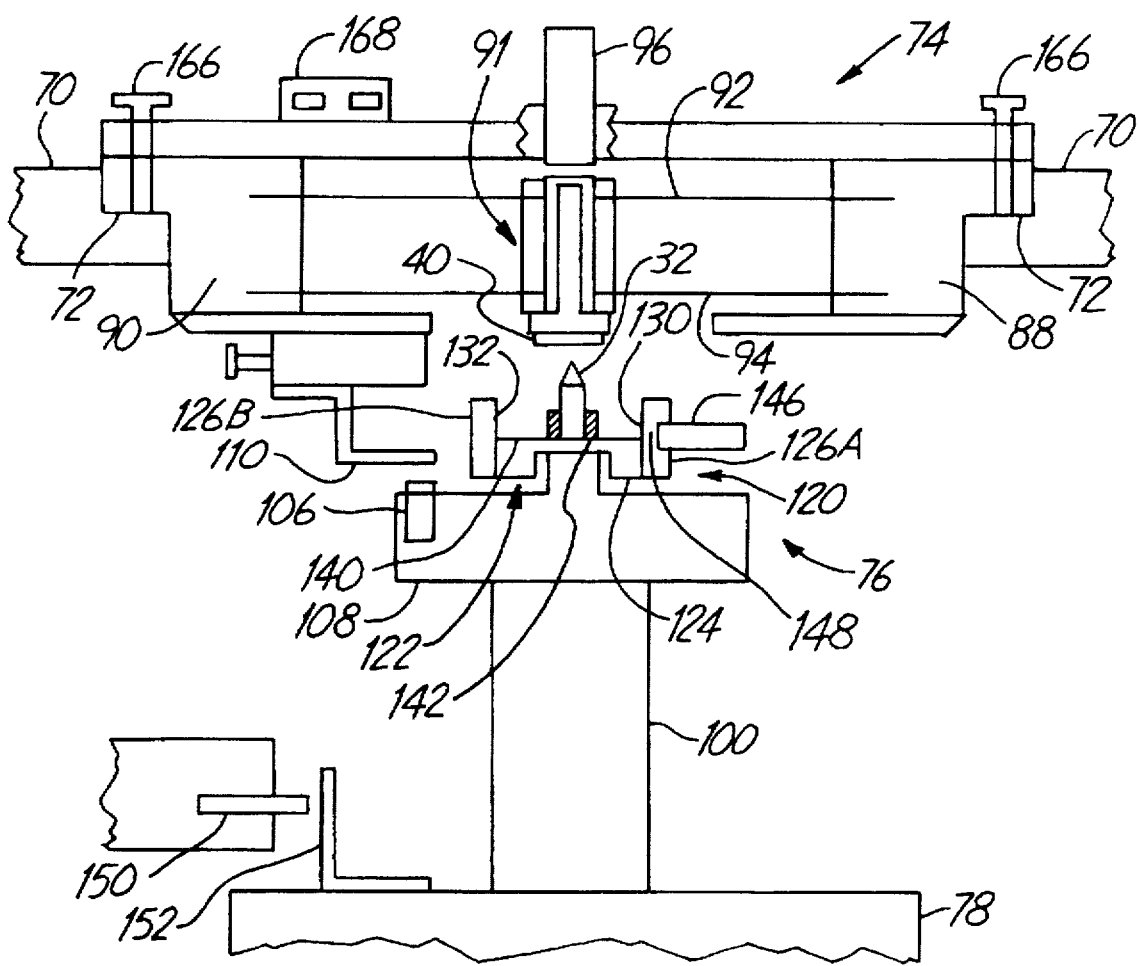
FIG. 10 is an enlarged portion of the system in FIG. 9.

Referring also to FIG. 10, the load cell assembly 74 includes support blocks indicated at 88 and 90 that rest upon the flanges 72 of the upper platform 70. A specimen mounting assembly 91 is supported between the support blocks 88 and 90 with two beryllium/copper (Be—Cu) diaphragm springs 92 and 94. The diaphragm springs 92 and 94 are compliant for vertical motions (Z direction) of the specimen mounting assembly 91. A suitable sensor 96, such as a capacitive transducer, senses vertical displacement of the specimen mounting assembly 91 and provides a representative signal to a signal recorder indicated at 98.

The indenter assembly 76 includes a piezoelectric transducer stack 100 to generate normal forces in the Z direction. The piezoelectric transducer stack 100 is driven by a voltage amplifier 102 forming part of a closed loop control system with power supplied from a DC power supply indicated at 104. Preferably, the indenter 32 is driven with a constant rate of displacement. A capacitive transducer 106 mounted to a support platform 108 of the indenter assembly 76 and referenced to a reference surface 110 of the load cell assembly 74 provides a signal representing total displacement of the indenter 32 in the Z direction. If desired, the indenter 32 can be driven as a function of a magnitude of the force applied to the thin film/substrate specimen 40 as measured by capacitive transducer 96. With the spring constant of the springs 92 and 94 known, the normal force applied to the thin film/substrate specimen 40 can be calculated.

The platform 108 is mounted to the piezoelectric transducer stack 100 and supports a lateral (horizontal) load cell indicated at 120. The lateral load cell 120 includes a support frame 122 having a base portion 124 and extending support arms indicated at 126A and 126B. Two diaphragm BE—CU springs 130 and 132 are joined to the extending arm portions 126A, 126B and the base portion 124 on opposite sides of the indenter 32. The springs 130 and 32 are substantially rigid for forces applied in the Z direction, but are substantially compliant for forces applied in the X direction. The springs 130 and 132 support and isolate a floating platform 140 from the frame 122. The floating platform 140 includes a suitable mounting assembly 142 used to secure the indenter 32 in a stationary position. A capacitive transducer 146 or other suitable sensor is mounted to the frame 122 to monitor displacement of the indenter 32 in the horizontal direction. As illustrated, a moveable capacitive sensor plate 148 is joined to the diaphragm 130 on a side opposite the floating platform 140. The capacitive transducer 146 provides a signal to the signal recorder 98 representing the distance or displacement of the floating platform 140 relative to the frame 122. With the spring constant of the springs 130 and 132 known, the lateral force applied to the thin film/substrate specimen can be calculated. A fourth capacitive transducer 150 mounted to the frame 66 and having a reference surface 152 mounted to the three-axis stage assembly 78 measures lateral displacement of the indenter 32 relative to the thin film/substrate specimen 40. A suitable computer 160 receives signals from the signal recorder 98 and controls the stage controller 98 and the D.C. power supply 104 during testing. FIGS. 9 and 10 are schematic in order to simplify understanding of the testing system 60. A suitable testing system having functional elements similar to the system 60 described above but without the indenter 32 of the present invention has been built by the IBM Research Division, Almaden Research Center of San Jose, Calif. and is described in "Microscratch and Load Relaxation Tests for Ultra-thin Films", J. Mater. Res. Vol. 6, No. 2, Feb 1991, pp.407–426, which is hereby incorporated by reference.

In the preferred embodiment, a tilting mechanism, embodied herein as a plurality of bolts 166, supports the load cell assembly 74 on the upper platform 70. The bolts 166 allow the load cell assembly 74 to be tilted about the X and Y axes so that the specimen 40 can be properly positioned proximate the indenter 32. A tilt sensor 168 disposed on the load cell assembly 74 measures and provides an indication as the orientation of the specimen 40.

Although the present invention has been described with reference to preferred embodiments, workers skilled in the art will recognize that changes may be made in form and detail without departing from the spirit and scope of the invention.

What is claimed is:

1. A method for measuring work of adhesion of a thin film to a substrate, the method comprising the steps of:
    preparing a specimen having a thin film joined to a major surface of a substrate;
    applying a force to a surface of the thin film, wherein the surface is in a plane intersecting with the major surface, and wherein the force is applied until a shear plane is created and separation of a portion of the thin film from the substrate occurs; and
    calculating a work of adhesion of the portion of the thin film as a function of the force.

2. The method of claim 1 and further comprising the steps of:
    measuring a magnitude of the force during the step of applying the force;
    measuring an area of the portion of the thin film separated from the substrate; and
    wherein the step of calculating includes calculating a work of adhesion of the portion of the thin film as a function of the magnitude of the force and the area of the portion of the substrate.

3. The method of claim 1 wherein the step of applying comprises engaging a block of material having a substantially flat surface engageable with the surface of the thin film, the substantially flat surface of the block of material having a width at least equal to a width of the surface of the thin film.

4. The method of claim 3 wherein the block of material includes a second substantially flat surface adjoining the first-mentioned substantially flat surface and forming a common edge of length at least equal to the width of the first-mentioned substantially flat surface.

5. The method of claim 4 wherein the block of material is wedge-shaped.

6. The method of claim 4 wherein the thin film is a hard material and the substrate is a hard material.

7. The method of claim 4 wherein the thin film is a ductile material and the substrate is a polymer.

8. The method of claim 3 wherein the step of applying the force includes applying a normal force to the thin film perpendicular to the major surface.

9. The method of claim 3 wherein the surface of the thin film is an edge surface extending from a major surface of the thin film toward the major surface of the substrate, the major surface of the thin film being parallel to the major surface of the substrate.

10. The method of claim 9 wherein the step of preparing includes preparing a specimen having a thin film joined to the substrate over a selected area; and wherein the step of applying includes separating the thin film from the substrate over the selected area.

11. The method of claim 10 wherein the step of preparing includes preparing a rectangular-shaped specimen having a selected length perpendicular to the width.

12. A method for measuring work of adhesion of thin film to a substrate, the method comprising the steps of:
    preparing a specimen having a thin film joined to a major surface of a substrate, the thin film having an upper surface facing away from the major surface;
    applying only a normal force to a selected width of the upper surface of the thin film until a shear plane is created by the normal force and separation of a portion of the thin film from the substrate occurs; and
    calculating a work of adhesion of the portion of the thin film as a function of the force.

13. The method of claim 12 and further comprising the steps of:
    measuring a magnitude of the normal force during the step of applying the normal force;
    measuring an area of the portion of the thin film separated from the substrate; and
    wherein the step of calculating includes calculating a work of adhesion of the portion of the thin film as a function of the magnitude of the normal force and the area of the portion of the substrate.

14. The method of claim 13 wherein the step of applying comprises engaging a block of material against the upper surface of the thin film.

15. The method of claim 14 wherein the block of material includes a substantially flat surface and the step of applying includes engaging the substantially flat surface against the upper surface of the thin film.

16. The method of claim 15 wherein the block of material includes a second substantially flat surface adjoining the first-mentioned substantially flat surface and forming a common edge of length at least equal to the width of the first-mentioned substantially flat surface.

17. The method of claim 16 wherein the block of material is wedge-shaped.

* * * * *